United States Patent [19]

Barillo et al.

[11] 3,959,185
[45] May 25, 1976

[54] PERFUME BLEND INCLUDING 2-KETO-6-SUBSTITUTED-DIOXANES-(1,4)

[75] Inventors: Joseph Barillo, Glen Rock; Thomas A. Payne, Jr., Teaneck; Warren J. Urban, River Vale, all of N.J.

[73] Assignee: Lever Brothers Company, New York, N.Y.

[22] Filed: Mar. 3, 1975

[21] Appl. No.: 554,940

Related U.S. Application Data

[62] Division of Ser. No. 452,229, March 18, 1974, abandoned.

[52] U.S. Cl. ............................. 252/522; 252/89 R; 424/69; 424/70; 426/536
[51] Int. Cl.[2] ..................... A61K 7/00; A61K 7/46; A61K 7/50
[58] Field of Search ................... 252/522; 260/340.2

[56] References Cited
UNITED STATES PATENTS
3,325,514  6/1967  Büchi ............................. 260/340.2

*Primary Examiner*—Jerome D. Goldberg
*Assistant Examiner*—A. P. Fagelson
*Attorney, Agent, or Firm*—Kenneth F. Dusyn; James J. Farrell; Arnold Grant

[57] ABSTRACT

Novel 2-keto-6-substituted dioxane-(1,4) compounds having the structural formula:

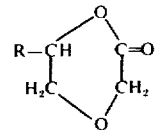

wherein R is an alkyl radical having 6–9 carbon atoms, mixtures thereof, and R'OCH$_2$ wherein R' is an alkyl radical having 5–8 carbon atoms. The novel compounds exhibit desirable fragrance and flavor properties.

5 Claims, No Drawings

PERFUME BLEND INCLUDING 2-KETO-6-SUBSTITUTED-DIOXANES-(1,4)

This is a division of application Ser. No. 452,229 filed Mar. 18, 1974 now abandoned.

BACKGROUND OF THE INVENTION

There is a continuing search for materials having desirable fragrance properties. Such materials are sought either to replace costly natural materials or to provide new fragrance or perfume types which have not heretofore been available. Especially desirable qualities for substances having interesting fragrances are stability in a wide variety of perfumed articles and perfume compositions, ease of manufacture and intensity of aroma.

The Prior Art

Insofar as applicants are aware, the 2-keto-6-alkyl and 6-(alkyloxymethyl)-dioxane-(1,4) disclosed and claimed in the instant application have not heretofore been known.

U.S. Pat. No. 3,280,065 relates to the preservation of latexes by incorporating 2-keto-6-methyl-dioxane-(1,4) and 2-keto-3-methyl-6-ethyl-dioxane-(1,4) into the latex to produce a latex composition stabilized against biological attack.

The Invention

The present invention relates to novel compounds which possess desirable odorous qualities and perfume-containing compositions containing these novel compounds as olfactory agents.

More particularly, the present invention provides novel 2-keto-6-alkyl and 6-substituted-dioxane (1,4) compounds of the formula:

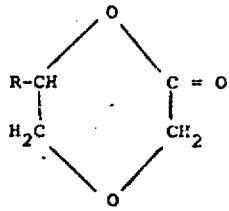

wherein R is an alkyl group of from $C_6$ to $C_9$, mixtures thereof and $R'OCH_2$—wherein R' is an alkyl group of from 5-8 carbon atoms. It has been discovered that these compounds possess desirable fragrance properties and are useful in perfume compositions. Typical of the compounds encompassed by the present invention are 2-keto-6-hexyl-dioxane-(1,4), 2-keto-6-heptyl-dioxane-(1,4), 2-keto-6-octyl-dioxane-(1,4), 2-keto-6-nonyl-dioxane-(1,4), 2-keto-6-($C_7$-$C_8$ alkyl-dioxane)-(1,4), 2-keto-6-($C_7$-$C_9$ alkyl)-dioxane-(1,4), 2-keto-6-(pentyloxymethyl)-dioxane-(1,4), 2-keto-6-(hexykloxymetyl)-dioxane-(1,4), 2-keto-6-(heptyloxylmethyl)-dioxane-(1,4), 2-keto-6-(octyloxymetyl)-dioxane-(1,4).

The 2-keto-6-substituted-dioxane-(1,4) compounds of this invention are olfactory agents and can be incorporated into a wide variety of compositions. The compounds can be added to perfume compositions in its pure form or it can be added to mixtures of materials in fragrance-imparting compositions to provide a desired fragrance character to a finished perfume material. The perfume and fragrance compositions obtained according to this invention are suitable in a wide variety of perfumed articles and can also be used to enhance, modify or reinforce natural fragrance materials.

The term "perfume composition" is used herein to mean a mixture of compounds including, for example, natural oils, synthetic oils, alcohols, aldehydes, ketones, esters, lactones, and frequently hydrocarbons which are admixed so that the combined odors of the individual components produce a pleasant or desired fragrance. Such perfume compositions or the novel compounds of this invention can be used in conjunction with carriers, vehicles, solvents, dispersants, emulsifiers, surface-active agents, aerosol propellants and the like.

In perfume compositions the individual components contribute their particular olfactory characteristics, but the overall effect of the perfume composition will be the sum effect of each ingredient. Thus, the 2-keto-6-substituted dioxane-(1,4) compounds of this invention can be used to alter the aroma characteristics of a perfume composition, for example, by high lighting or moderating the olfactory reaction contributed by another ingredient of the composition.

The amount of 2-keto-6-substituted-dioxane-(1,4) compound of this invention which will be effective in perfume compositions depends on many factors including the other ingredients, their amounts and the effects which are desired. It has been found that perfume compositions containing as little as 0.01 to 2% by weight of mixtures or compounds of this invention, or even less can be used to impart a pleasant odor to soaps, cosmetics and other products. The amount employed will depend on considerations of cost, nature of end product, the effect desired in the finished product, and the particular fragrance sought.

The keto-6-substituted-dioxane-(1,4) compounds disclosed herein can be used alone in fragrance-modifying composition, or in a perfume composition as an olfactory component in detergents and soaps; space deodorants; perfumes; colognes; bath preparations such as bath oil, bath salts; hair preparations such as lacquers; brilliantives, pomades, and shampoos; cosmetic preparations such as creams, deodorants, hand lotions, sun screens; powders such as talcs, dusting powders, face powder and the like. When the compound of this invention are used in perfumed articles such as the foregoing, it can be used in amounts of 0.1% or lower. Generally, it is preferred not to use more than about 2.0% in the finished perfumed article, since the use of too much will tend to unbalance the total aroma and will needlessly raise the cost of the article.

The novel 2-keto-6-alkyl-dioxane-(1,4) compounds of the present invention can be prepared by reacting an alkali metal alcoholate of a 1,2-alkanediol with a monohalogenated acetic acid to form the intermediate compound, alkali metal carboxymethyl-2-hydroxyalkyl ether. The 2-keto-6-alkyl-dioxane-(1,4) is obtained from the intermediate alkali metal carboxymethyl-2-hydroxyalkyl ether by cyclizing under acidic conditions.

The 1,2-alkanediol reactants useful for the preparation of the novel compounds of the present invention can be any 1,2-diol having the structure:

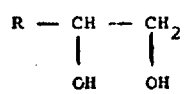

wherein R is an alkyl radical having 6–9 carbon atoms and mixtures thereof. Illustrative examples of the 1,2-alkanediol reactant include 1,2-octanediol, 1,2-nonanediol, 1,2-decanediol, and 1,2-undecanediol. The alkali metal alcoholate of the 1,2-alkanediols are prepared by action of alkali metal hydroxides, for example, sodium hydroxide and potassium hydroxide on the diol. The 1,2-alkanediols can be prepared by known methods. In one known technique, 1,2-alkanediols are prepared from the corresponding 1-alkene oxide or alpha-olefin epoxides by treating the oxide with water containing a catalytic amount of mineral acid.

Any monohalogenated acetic acid may be employed as the reactant, but chloroacetic acid and bromoacetic acid are preferred, particularly the former.

The alkali metal alcoholate of 1,2-alkanediol is prepared in situ by adding powdered alkali metal hydroxide, for example, sodium hydroxide or potassium hydroxide, to 1,2-alkanediol. Approximately 2 moles of alkali metal hydroxide is employed per mole of alkanediol. The addition of the alkali metal hydroxide to the diol is carried out with vigorous stirring. The compounds react very easily and the reaction is conducted at room temperature or at slightly elevated temperature, for example, 40°–50°C.

Reaction of the monohalogenated acetic acid with the alkali metal alcoholate of the 1,2-alkanediol is carried out by slowly adding the acetic acid reagent to the alcoholate diol. The addition is conducted at a slightly elevated temperature, for example, 50°–60°C and the reaction is maintained at this temperature until completion. Approximately equimolar proportions of the reactants is employed for this reaction. The reaction product is the alkali metal carboxymethyl 2-hydroxyalkyl ether. This compound is extracted from the reaction mixture with a suitable solvent, for example pet ether, ethyl ether, ethyl acetate, benzene. The desired product, 2-keto-6-alkyl-dioxane-(1,4), is prepared from the above-mentioned ether compound by cyclizing with a mineral acid such as hydrochloric acid, sulfuric acid, phosphoric acid. The final product is isolated by distillation under reduced pressure.

The novel 2-keto-6-(alkyloxymethyl)-dioxane-(1,4) compounds of the present invention can be prepared by reacting an alkali metal alcoholate of a glycerol monoalkyl ether with a monohalogenated acetic acid.

The glycerol monoalkyl ethers that can be employed in preparing the novel compounds of this invention have the structure:

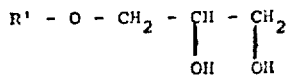

wherein R' is an alkyl radical having 5–8 carbon atoms. Illustrative examples of the monoalkyl ether glycerols include glycerol monopentyl ether, glycerol monohexyl ether, glycerol monoheptyl ether, and the monooctyl ether of glycerol. The glycerol ethers can be prepared by methods well known in the art. One method employs the addition of the appropriate alcohol to epichlorohydrin. The reaction is catalyzed by stannous chloride. The epichlorohydrin is slowly added to the alcohol at an elevated temperature, for example, 80°–90°C and maintained at the temperature for about 1 hour. Cool the reaction mixture to room temperature or below and add an equimolar amount of sodium hydroxide to convert the chlorohydrin to the corresponding epoxide. The reaction mixture is heated to reflux after adding water, sulfuric acid, and sufficient acetone to form a homogeneous solution. After neutralizing the reaction mixture the glycerol monoalkyl ether is isolated by extracting with pet ether and distilling the product under reduced pressure.

The method for preparing 2-keto-6(alkyloxymethyl-dioxane-(1,4) from the alkali metal alcoholate of glycerol monoalkyl ether and a monohalogenated acetic acid is the same as described above for the 2-keto-6-alkyl-dioxane-(1,4) compounds.

The 2-keto-6-substituted-dioxane-(1,4) compound of the present invention find particular utility in detergent compositions. The dioxanes may if desired be employed as the sole perfume ingredient, but normally will be used as component of a blend of perfume oils to impart a desirable modification to the blend. The novel dioxanes are stable toward all of the substances customarily employed in neutral or acidic detergent compositions.

The detergent compositions wherein the 2-keto-6-substituted-dioxanes-(1,4) are useful may comprise any surfactant species, whether anionic, cationic, nonionic, or amphoteric, including the soaps. All of the usual builder substances may be employed, such as the polyphosphates, orthophosphates, carbonates, citrates, oxydiacetates, oxydisuccinates, carboxymethyloxysuccinates, etc. Oxidizing agents, such as the perborates, hypochlorites, dichlorocyanurates, etc. have no effect on the odor of the 2-keto-6-substituted-dioxane-(1,4) compounds when employed together in detergent or dry bleach compositions.

When employed in admixture with other perfume components, the proportion of 2-keto-6-substituted-dioxane-(1,4) may range from about 1 to about 99%, on the mixture basis. A preferred range is about 10 to about 90%, and most generally a mixture will contain about 20 to about 75% of the dioxane compound by weight.

When a perfume blend containing one or more 2-keto-6-substituted-dioxanes-(1,4) in the useful proportions set forth herein is employed in a detergent or soap composition, the proportion of 2-keto-6-substituted-dioxanes-(1,4) in the total composition will usually vary from about 0.001 to about 2%, by weight.

The selection of any particular component or proportion thereof of a detergent or soap composition wherein a 2-keto-6-substituted-dioxane-(1,4) is to be incorporated will depend upon the detergency effect desired, and forms no part of the present invention.

Suitable detergent or soap compositions may be in any of the usual forms, particulate, liquid, bar, or briquette. Shampoo compositions are suitable, and may be based on soaps or nonsoap detergents.

Suitable soap and nonsoap detergent species, builders to enhance detergency, and miscellaneous adjuvants are discussed in the texts, "Surface Active Agents" by Schwartz and Perry, and "Surface Active Agents and Detergents" by Schwartz, Perry and Berch, both Interscience Publishers, New York, N. Y., the disclosures of both being incorporated herein by reference.

Suitable particulate detergent compositions are disclosed in U.S. Pat. Nos. 2,829,102, 2,829,108 and 3,188,291, paticulate soap compositions in U.S. Pat. Nos. 2,329,694 and 2,940,935, detergent tablets in U.S. Pat. Nos. 3,055,837, 3,043,779 and 2,894,912, soap tablets in U.S. Pat. Nos. 2,404,298, 2,649,417, 2,215,539 and 3,284,363, liquid detergent compositions in U.S. Pat. Nos. 2,941,950 and 3,052,635 and shampoos in U.S. Pat. Nos. 3,086,943 and 3,263,733, all of which are incorporated herein by reference.

EXAMPLE 1

Preparation of 2-keto-6-hexyl-dioxane-(1,4)

A homogeneous clear solution is prepared by adding 3 moles of acetone to 1 mole of octene (1,2) oxide at room temperature. After adding 50 grams of 5% aqueous sulfuric acid to the solution, the acetone is evaporated off and the resulting solution is neutralized by adding an aqueous sodium hydroxide. The neutralized solution is extracted with pet ether and the extract dried over anhydrous magnesium sulfate. The pet ether is stripped off and 1,2-octanediol is obtained by distilling under vacuo, b.p. 103°–105°C/0.2 mm.

Two moles of powdered sodium hydroxide is added to 1 mole (146g) of 1,2-octanediol with vigorous stirring at room temperature. During the addition of the base, the temperature of the reaction mixture increases from room temperature to about 40°–50°C and the reaction mixture becomes a thick pasty mass. One mole of monochloroacetic acid is slowly added to the reaction mixture while the temperature is maintained between 50°–55°C. The reaction mixture is then stirred for 1.5 hours at 50°–60°C. After cooling to room temperature, the reaction mixture is extracted with pet ether; the extracts are acifified with concentrated hydrochloric acid and then dried over anhydrous magnesium sulfate. The pet ether is removed and 2-keto-6-hexyl-dioxane-(1,4) is distilled at reduced temperature, b.p. 90°–111°C/0.2 mm.

The novel 2-keto-6-hexyl-dioxane-(1,4) compound has an aldehydic, wood and wholesome odor.

The infra red spectrum of 2-keto-6-hexyl-dioxane-(1,4) exhibited the following peaks:

| | | |
|---|---|---|
| 5.75 $\mu$ | 1750 cm$^{-1}$ | (strong) |
| 7.05 $\mu$ | 1420 cm$^{-1}$ | (weak) |
| 7.45 $\mu$ | 1340 cm$^{-1}$ | (moderate) |
| 9.1 $\mu$ | 1110 cm$^{-1}$ | (strong) |
| 10.7 $\mu$ | 935 cm$^{-1}$ | (strong) |
| 8.0 $\mu$ | 1250 cm$^{-1}$ | (strong) |
| 8.25 $\mu$ | 1215 cm$^{-1}$ | (strong) |

EXAMPLE 2

Preparation of 2-keto-6-octyl-dioxane-(1,4)

A homogeneous clear solution is prepared by adding 3 moles of acetone to 1 mole of 1-decene oxide at room temperature. After adding 50 grams of 5% aqueous sulfuric acid to the solution, the acetone is evaporated off and the resulting solution is neutralized by adding an aqueous sodium hydroxide. The neutralized solution is extracted with pet ether and the extract dried over anhydrous magnesium sulfate. The pet ether is stripped off and 1,2-decanediol is obtained by distilling under vacuo.

Two moles of powdered sodium hydroxide is added to 1 mole (174g) of 1,2-decanediol with vigorous stirring at room temperature. During the addition of the base, the temperature of the reaction mixture increases from room temperature to about 40°–50°C and the reaction mixture becomes a thick pasty mass. One mole of monochloroacetic acid is slowly added to the reaction mixture while the temperature is maintained between 50°–55°C. The reaction mixture is then stirred for 1.5 hours at 50°–60°C. After cooling to room temperature, the reaction mixture is extracted with pet ether; the extracts are acifified with concentrated hydrochloric acid and then dried over anhyerous magnesium sulfate. The pet ether is removed and 2-keto-6-octyl-dioxane-(1,4) is distilled at reduced temperature, b.p. 150°C/2.4 mm. The compound exhibited a peachy lactone aroma.

EXAMPLE 3

Preparation of 2-keto-6-C$_7$–C$_8$ alkyl-dioxane-(1,4)

A homogeneous clear solution is prepared by adding 3 moles of acetone to 1 mole of a mixture of 1-nonene oxide and 1-decene oxide at room temperature. After 50 grams of 5% aqueous sulfuric acid to the solution, the acetone is evaporated off and the resulting solution is neutralized by adding an aqueous sodium hydroxide. The neutralized solution is extracted with pet ether and the extract dried over anhydrous magnesium sulfate. The pet ether is stripped off and a mixture of 1,2-nonanediol and 1,2-decanediol is obtained by distilling under vacuo.

Two moles of powdered sodium hydroxide is added to 1 mole of a mixture of 1,2-nonanediol and 1,2-decanediol with vigorous stirring at room temperature. During the addition of the base, the temperature of the reaction mixture increases from room temperature to about 40°–50°C and the reaction mixture becomes a thick pasty mass. One mole of monochloroacetic acid is slowly added to the reaction mixture while the temperature is maintained between 50°–55°C. The reaction mixture is then stirred from 1.5 hours at 50°–60°C. After cooling to room temperature, the reaction mixture is extracted with pet ether; the extracts are acidified with concentrated hydrochloric acid and then dried over anhydrous magnesium sulfate. The pet ether is removed and 2-keto-6-C$_7$–C$_8$ alkyl dioxane-(1,4) is distilled at reduced temperature, b.p. 123°–150°C/0.2-0.9 mm. This compound exhibits an aroma described as "aldehydic with an oily background note."

EXAMPLE 4

Preparation of 2-keto-6-C$_7$–C$_9$-dioxane-(1,4)

A homogeneous clear solution is prepared by adding 3 moles of acetone to a (1:1:1) mixture of 1-nonene oxide, 1-decene oxide, and 1-undecene oxide at room temperature. After adding 50 grams of 5% aqueous sulfuric acid to the solution, the acetone is evaporated off and the resulting solution is neutralized by adding an aqueous sodium hydroxide. The neutralized solution is extracted with pet ether and the extract dried over anhydrous magnesium sulfate. The pet ether is stripped off and a mixture of 1,2-nonanediol, 1,2-decanediol and 1,2 undecanediol is obtained by distilling under vacuo.

Two moles of powdered sodium hydroxide is added to 1 mole of a mixture of 1,2-nonanediol, 1,2-decanediol and 1,2-undecanediol with vigorous stirring at room temperature. During the addition of the base, the temperature of the reaction mixture increases from room temperature to about 40°–50°C and the reaction mixture becomes a thick pasty mass. One mole of monochloroacetic acid is slowly added to the reaction mixture while the temperature is maintained between 50°–55°C. The reaction mixture is then stirred for 1.5 hours at 50°–60°C. After cooling to room temperature, the reaction mixture is extracted with pet ether; the extracts are acifified with concentrated hydrochloric acid and then dried over anhydrous magnesium sulfate. The pet ether is removed and 2-keto-6-C$_7$–C$_9$-dioxane- (1,4) is distilled at reduced temperature.

The novel compound possesses a "peachy" and fresh "odor."

EXAMPLE 5

Preparation of 2-keto-6-(octyloxymethyl)-dioxane-(1,4)

One mole (92.5g) of epichlorohydrin is added over 1 hour to 1 mole (132g) 1-octanol containing a catalytic amount of stannous chloride. The addition is carried out at a temperature of about 90°C, and after the addition is completed the reaction mixture is maintained at 90°C for about 1 hour. The reaction is allowed to cool to room temperature; about 3 moles of water are added and sulfuric acid is then added to the reaction. Sufficient acetone is added to form a homogeneous solution and then the reaction is heated at reflux for about 1 hour. Cool the reaction mixture to room temperature or below and add an equimolar amount of sodium hydroxide to convert the chlorohydrin to the corresponding epoxide. The acetone is then evaporated off and the resulting mixture is neutralized with aqueous sodium hydroxide. The neutralized solution is extracted with pet ether and the extract is dried over anhydrous magnesium sulfate. The pet ether is removed and the monooctylether of glycerol is obtained by distilling under vacuo.

Two moles of powdered sodium hydroxide is added to 1 mole of monooctylether of glycerol with vigorous stirring at room temperature. During the addition of the base, the temperature of the reaction mixture increases from room temperature at about 40°–50°C and the reaction mixture becomes a thick pasty mass. One mole of monochloroacetic acid is slowly added to the reaction mixture while the temperature is maintained between 50°–55°C. The reaction mixture is then stirred for 1.5 hours at 50°–60°C. After cooling to room temperature, the reaction mixture is extracted with pet ether; the extracts are acidified with concentrated hydrochloric acid and then dried over anhydrous magnesium sulfate. The pet ether is removed and 2-keto-6-(octyloxymethyl)-dioxane-(1,4) is distilled at reduced temperature.

The following compounds are prepared according to the procedure above:

2-keto-6-(pentyloxymethyl)dioxane-(1,4)
2-keto-6-(hexyloxymethyl)dioxane-(1,4)
2-keto-6-(heptyloxymethyl)dioxane-(1,4)

by employing amyl alcohol, 1-hexanol, and 1-heptanol, respectively in place of 1-octanol.

Each of the above compounds exhibited a typical lactone aroma.

The foregoing description of the present invention has been presented describing certain operable and preferred embodiments. It is not intended that the invention should be so limited, since variations and modifications thereof will be obvious to those skilled in the art, all of which are within the spirit and scope of this invention.

What is claimd is:

1. A perfume blend including an olfactorily effective amount of a compound having the formula:

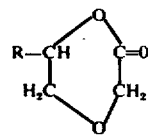

wherein R is R'OCH$_2$— wherein R' is an alkyl radical of from C$_5$–C$_8$.

2. The perfume blend of claim 1 wherein R' is C$_5$.
3. The perfume blend of claim 1 wherein R' is C$_6$.
4. The perfume blend of claim 1 wherein R' is C$_7$.
5. The perfume blend of claim 1 wherein R' is C$_8$.

* * * * *